United States Patent
Robertsson et al.

(10) Patent No.: US 10,961,552 B2
(45) Date of Patent: Mar. 30, 2021

(54) PROCESS FOR THE PRODUCTION OF AN ORGANIC ACID FROM A LIGNOCELLULOSIC FEEDSTOCK

(71) Applicant: RISE INNVENTIA AB, Stockholm (SE)

(72) Inventors: Victor Robertsson, Stockholm (SE); Niklas Berglin, Täby (SE); Mikael Jansson, Skogås (SE)

(73) Assignee: RISE INNVENTIA AB, Stockholm (SE)

( * ) Notice: Subject to any disclaimer, the term of this patent is extended or adjusted under 35 U.S.C. 154(b) by 127 days.

(21) Appl. No.: 16/332,063

(22) PCT Filed: Sep. 6, 2017

(86) PCT No.: PCT/SE2017/050883
§ 371 (c)(1),
(2) Date: Mar. 11, 2019

(87) PCT Pub. No.: WO2018/052359
PCT Pub. Date: Mar. 22, 2018

(65) Prior Publication Data
US 2019/0367955 A1    Dec. 5, 2019

(30) Foreign Application Priority Data
Sep. 13, 2016   (EP) ..................................... 16188531

(51) Int. Cl.
| | |
|---|---|
| C12P 7/56 | (2006.01) |
| C12P 7/40 | (2006.01) |
| C12P 7/42 | (2006.01) |
| C12P 7/46 | (2006.01) |
| C12P 7/48 | (2006.01) |
| C12P 7/50 | (2006.01) |
| C12P 7/52 | (2006.01) |
| C12P 7/54 | (2006.01) |
| C12P 7/58 | (2006.01) |
| C12P 13/14 | (2006.01) |
| C13K 1/02 | (2006.01) |
| D21C 1/06 | (2006.01) |

(52) U.S. Cl.
CPC .................. *C12P 7/56* (2013.01); *C12P 7/40* (2013.01); *C12P 7/42* (2013.01); *C12P 7/46* (2013.01); *C12P 7/48* (2013.01); *C12P 7/50* (2013.01); *C12P 7/52* (2013.01); *C12P 7/54* (2013.01); *C12P 7/58* (2013.01); *C12P 13/14* (2013.01); *C13K 1/02* (2013.01); *D21C 1/06* (2013.01)

(58) Field of Classification Search
CPC ......... Y02E 50/10; Y02E 50/14; Y02E 50/30; Y02E 50/32; Y02E 50/16; D21C 11/0007; D21C 3/20; D21C 3/02; D21C 3/04; D21C 1/06; C07C 29/88; C07C 41/44; C07C 45/85; C10G 1/00; C10G 1/04; C10G 1/086; C10G 1/10; C10G 2300/1003; C10G 2300/1014; C10G 3/00; C10L 1/02; C10L 2200/0469; C10L 2290/06; C10L 2290/24; C10L 2290/544; C10L 2290/547; C10L 3/00; C10L 5/442; C10L 5/48; C12P 7/08; C12P 7/10; C12P 7/40; C12P 2201/00; C12P 2203/00; C12P 13/14; C12P 19/02; C12P 7/42; C12P 7/46; C12P 7/48; C12P 7/50; C12P 7/52; C12P 7/54; C12P 7/56; C12P 7/58; Y02P 20/582; Y02P 30/20; Y02P 40/40; Y02P 4/44; Y02P 20/127; Y02P 20/10; C13K 1/02; C01F 11/46; C08B 37/0057; C08B 3/00; C08H 6/00; C08H 8/00
See application file for complete search history.

(56) References Cited

U.S. PATENT DOCUMENTS

| | | | |
|---|---|---|---|
| 2009/0226979 A1 | 9/2009 | Retsina et al. | |
| 2011/0003352 A1* | 1/2011 | Retsina | C08H 8/00 435/136 |
| 2011/0314726 A1* | 12/2011 | Jameel | C12P 7/10 44/451 |
| 2014/0024093 A1* | 1/2014 | Blackbourn | D21C 3/20 435/158 |

(Continued)

FOREIGN PATENT DOCUMENTS

| | | |
|---|---|---|
| WO | 0017378 A2 | 3/2000 |
| WO | 2009025547 A1 | 2/2009 |
| WO | 2011022644 A2 | 2/2011 |
| WO | 2018052359 A1 | 3/2018 |

OTHER PUBLICATIONS

Suan Shi et al, "Production of Lactic Acid from the Mixture of Softwood Pre-Hydrolysate and Paper Mill Sludge by Simultaneous Saccharification and Fermentation"; Appl Biochem Biotechnol (2015) 175; Jan. 6, 2015, pp. 2741-2754, DOI 10.007/s12010-014-1451-8.

(Continued)

*Primary Examiner* — Deborah K Ware
(74) *Attorney, Agent, or Firm* — Pearne & Gordon LLP (57) ABSTRACT

Process for the production of an organic acid from a lignocellulosic feedstock. The process is integrated with a pulp mill and comprises: a) pre-treating a lignocellulosic feedstock with an alkaline liquor from the pulp, thereby obtaining a pretreated cellulosic feed and a black liquor; b) subjecting the pretreated cellulosic feed from step a) to enzymatic hydrolysis, thereby obtaining a saccharide feed; c) subjecting the saccharide feed from step b) to microbial fermentation using calcium oxide from the pulp mill as a neutralising agent, thereby obtaining an organic acid calcium salt; d) treating the organic acid calcium salt with sulfuric acid, thereby obtaining the organic acid; e) optionally isolating lignin from the black liquor obtained in step a), thereby obtaining lignin and weak black liquor; and f) returning the black liquor from step a) and/or the weak black liquor from step e) to the pulp mill chemical recovery process.

16 Claims, 5 Drawing Sheets

(56) References Cited

U.S. PATENT DOCUMENTS

2015/0072389 A1* 3/2015 Retsina ............... C12P 7/40
                                                   435/165
2017/0226695 A1* 8/2017 Rowlands ............ C07C 41/44

OTHER PUBLICATIONS

Jacob R. Borden, et al., "Simultaneous Saccharification and Fermenttion of Cellulosic Biomass to Acetic Acid"; Applied Biochemistry and Biotechnology, 2000, pp. 963-970, vol. 84-86, XP008087559.
Aloia Romaní, "SSF production of lactic acid from cellulosic biosludges", Bioresource Technology 99 (2008), pp. 4247-4254, Oct. 24, 2007.
European Search Report and Form 1703 issued in Application No. EP 16188531 dated Mar. 7, 2017; 4 pages.
Written Opinion and International Search Report issued in application No. PCT/SE2017/050883 dated Nov. 23, 2017; 11 pages.

* cited by examiner

PROCESS FOR THE PRODUCTION OF AN ORGANIC ACID FROM A LIGNOCELLULOSIC FEEDSTOCK

TECHNICAL FIELD

The present disclosure relates to the field of biomass valorisation and more specifically to the production of organic acids from biomass by saccharification and fermentation.

BACKGROUND ART

In order to achieve a sustainable society it is in the long-term necessary to replace fossil-based materials, such as fuels, commodity- and specialty chemicals, with materials from renewable sources. This has resulted in an increasing focus on, and prevalence of, bio-based production of chemicals.

Organic acids such as lactic acid are among chemicals already commonly produced from renewable sources. Today, large-scale production of lactic acid is performed by microbial fermentation of feedstocks comprising oligosaccharides or starches, such as corn, beet sugar or cane sugar. Lactic acid is a platform chemical that can be used to produce products such as polylactic acid (PLA), an increasingly prevalent biodegradable thermoplastic polymer.

The use of starchy feedstocks requires diverting the use of cropland and therefore competes with food production. Therefore, there is a general desire in the field of bio-based materials to develop next generation methods which utilize non-food biomass such as forestry materials, grasses or waste materials from food processing as raw materials.

WO 2009/025547 describes a method for the production of an organic acid as a fermentation product from lignocellulosic biomass. The method comprises the steps of pretreatment of the lignocellulosic biomass with an alkaline agent; simultaneous saccharification and fermentation (SSF) of the pretreated lignocellulosic biomass; and optionally recovery of the fermentation product. The lignocellulosic biomass is selected from the group consisting of grass, wood, bagasse, straw, paper, plant material, and combinations thereof.

US 2009/0226979 discloses a method for hydrolyzing cellulosic material into sugars using the spent liquor media from a pulping process or from another cellulosic biomass process.

There remains a need for improved processes for producing organic acids, such as lactic acid or acetic acid, from lignocellulosic feedstocks.

SUMMARY OF THE INVENTION

The inventors of the present invention have identified a number of deficiencies associated with prior art methods for the production of organic acids such as lactic acid and acetic acid from lignocellulosic feedstocks. In order to obtain a suitable yield of product organic acids, a pretreatment step is required, but this pretreatment requires the use of substantial amounts of alkaline liquor. Such a pretreatment is expensive, making prior-art methods commercially less viable. Moreover, the process for producing organic acids generates large amounts of waste products that require disposal.

It is thus an object of the present invention to provide a process for the production of an organic acid from a lignocellulosic feedstock, the said process having a greater economic viability and a more benign environmental impact as compared to prior art methods.

This object is achieved by a process for the production of an organic acid from a lignocellulosic feedstock according to the appended claims. The process is integrated with a pulp mill and comprises the steps:

a) providing a lignocellulosic feedstock;
b) obtaining an alkaline liquor from the pulp mill;
c) pre-treating the lignocellulosic feedstock with the alkaline liquor, thereby obtaining a pretreated cellulosic feed and a black liquor;
d) obtaining calcium oxide from the pulp mill;
e) subjecting the pretreated cellulosic feed from step c) to enzymatic hydrolysis, thereby obtaining a saccharide feed;
f) subjecting the saccharide feed from step e) to microbial fermentation using the calcium oxide from step d) as a neutralising agent, thereby obtaining an organic acid calcium salt;
g) treating the organic acid calcium salt with sulfuric acid, thereby obtaining gypsum and the organic acid;
h) optionally isolating lignin from the black liquor obtained in step c), thereby obtaining lignin and weak black liquor; and
i) returning the black liquor obtained in step c) and/or the weak black liquor obtained in step h) to the pulp mill for integration with the pulp mill chemical recovery process;
wherein steps e) and f) are performed either sequentially or simultaneously.

By obtaining the alkaline liquor from the pulp mill in step b) and returning the spent alkaline liquor to the pulp mill chemical recovery process in step i), the liquor can be regenerated and reused in either the pulp mill processes and/or the organic acid production process. Therefore, the cost of alkaline pretreatment and the amount of waste produced during the production of organic acid is substantially reduced, making the process for the production of organic acids more viable from a commercial and environmental standpoint.

Steps e) and f) may be performed simultaneously, i.e. as a simultaneous saccharification and fermentation step. This simplifies the process, reducing the number of operations and requirement for equipment, and may potentially increase the yield of the organic acid product.

The organic acid produced by the process may be lactic acid, acetic acid, citric acid, itaconic acid, succinic acid, fumaric acid, glycolic acid, pyruvic acid, acetic acid, glutamic acid, malic acid, maleic acid, propionic acid, butyric acid, gluconic acid or combinations thereof. Any of these acids may be produced by saccharificaton and fermentation of a lignocellulosic feedstock by appropriate selection of the fermentation microorganisms. The organic acid produced by the process is preferably lactic acid or acetic acid, even more preferably lactic acid.

The alkaline liquor used in the pre-treatment step c) may comprise or consist of pulp mill white liquor and/or soda liquor. White liquor is abundantly available in kraft pulp mills and is highly suitable for the fractionation and pretreatment of lignocellulosic feedstocks. Soda liquor is readily available as the pulping liquor in soda pulp mills, as NaOH make-up in Kraft pulp mills, or by electrolysis of electrostatic precipitator dust.

The alkaline liquor used in the pre-treatment step c) may be in part derived from electrolysis of pulp mill electrostatic precipitator (EP) dust. The sulfuric acid used in step g) may also be derived from electrolysis of pulp mill electrostatic precipitator dust. By utilising EP dust, a pulp mill waste product is converted to two process chemicals necessary for the production of the organic acid. This reduces the amount of waste produced by the integrated process and also reduces the quantities of "make-up" chemicals required for the pulp mill and organic acid production processes.

The alkaline liquor may be essentially free from sodium sulfide. Such an alkaline liquor may be obtained by the electrolysis of pulp mill electrostatic precipitator (EP) dust as described above. By using liquor free from sodium sulfide in the pre-treatment step, lignin that is essentially free from sulfur may be obtained from the resulting hydrolysate (black liquor).

The black liquor obtained in step c) may be combined with pulp mill black liquor prior to isolating lignin in step h). By isolating lignin from the black liquor of the organic acid production process, the pulp mill process, or both, a number of advantages are obtained. A potentially valuable product, lignin, is obtained from a waste stream, and at the same time the mass of waste being provided to the pulp mill recovery boiler is reduced, thus increasing the capacity of the pulp mill and/or organic acid production process.

At least a portion of the gypsum obtained in step g) may be returned to the pulp mill for integration with a pulp mill lime regeneration process. By regenerating calcium oxide from the gypsum by-product the amount of waste produced by the organic acid production process is reduced and the amount of calcium oxide make-up required by the pulp mill and/or organic acid production process is also reduced. This favourably improves the overall process economics.

The lignocellulosic feedstock from step a) may be subjected to an aqueous prehydrolysis step prior to step b), thereby obtaining a prehydrolysed lignocellulosic feedstock and a hemicellulose hydrolysate. This allows a relatively pure hemicellulose-rich fraction to be obtained directly. A hemicellulose, such as xylan, or a product derived from hemicellulose, such as xylose or furfural, may be isolated from the hemicellulose hydrolysate. This enables further valorisation of the hemicellulose component of the lignocellulosic feedstock.

The organic acid obtained in step g) may be purified by reactive distillation with an alcohol to provide an ester, followed by hydrolysis of the ester to provide a purified organic acid. Since the alcohol can be easily recycled, the reactive distillation is a simple, resource-effective means of obtaining a purified organic acid.

The pretreated cellulosic feed from step c) may be subjected to an oxygen delignification step prior to step e). In some cases this may increase the yield of the organic acid and/or reduce the need for further purification of the organic acid obtained by saccharification and fermentation.

At least part of the pretreated cellulosic feed from step c) may be subjected to neutralisation by addition of sulfuric acid prior to step e). This allows the saccharification and fermentation steps to be performed at an optimal pH, increasing the rate and yield of product formation.

The lignocellulosic feedstock may be selected from the group consisting of wood, grass, bagasse, straw, plant material, paper, and combinations thereof. Such materials include, but are not limited to, pulpwood, forestry residues, energy cane, and mixtures thereof.

The pretreated cellulosic feed obtained in step c) may comprise or consist of pulp stock obtained from the regular pulping process stream of a pulp mill; i.e. steps a) to c) may be performed as part of the usual pulp mill operation using the usual pulp mill feedstock. Such a process integration may for example be used to reduce expenditure on capital equipment upon setting up production of an organic acid.

The pretreated cellulosic feed obtained in step c) may comprise or consist of material produced entirely separately from the regular pulping process stream of a pulp mill; i.e. steps a) to c) are performed separately from the usual pulp mill operation using a separate feedstock. This allows a greater flexibility in the choice of lignocellulosic feedstock and may for example allow the use of a cheaper feedstock. For example, the lignocellulosic feedstock may comprise or consist of material that has been or would be rejected as feedstock in the normal pulp mill operation, such as for example forestry residues and energy cane. This may reduce the cost of the lignocellulosic feedstock, may reduce the load on the pulp mill bark boiler, and may provide a use for materials that otherwise may be of limited use in chemical production.

The pretreated lignocellulosic feedstock may comprise or consist of mixtures of pulp mill pulp stock and material produced entirely separately from the pulping process stream of a pulp mill.

All filtrates and residues from the organic acid production process may be returned to the pulp mill and integrated with the pulp mill chemical and/energy recovery processes. Thus, the organic acid production process may be fully integrated with pre-existing pulp mill processes. Since a modern pulp mill is essentially a closed-loop system, this makes highly efficient use of the input materials to the organic acid production process, since nearly all materials are utilised in chemical regeneration or energy generation.

The pulp mill may be an alkaline pulp mill, preferably a kraft pulp mill or soda pulp mill, even more preferably a kraft pulp mill. Kraft pulping if the predominant form of pulping in use, and therefore the organic acid production process is readily integrated with the majority of paper mills in operation.

Further aspects, objects and advantages are defined in the detailed description below with reference to the appended drawings.

BRIEF DESCRIPTION OF THE DRAWINGS

For the understanding of the present invention and further objects and advantages of it, the detailed description set out below can be read together with the accompanying drawings, in which the same reference notations denote similar items in the various diagrams, and in which.

DETAILED DESCRIPTION

The process according to the present invention is performed in close integration with a pulp mill, preferably an alkaline pulp mill, such as a kraft pulp mill or soda pulp mill, and even more preferably a kraft pulp mill. The chemicals required for the process of the invention are readily available or obtainable from the pulp mill, and the waste and residue streams can be returned to the pulp mill for regeneration of the required chemicals.

Rising wood and energy costs make it increasingly urgent for the forest-based industry to find by-product uses with higher market value. Pulp mills have unique prerequisites to make large volumes of value-added bio-based materials and chemicals in parallel with pulp production. A modern kraft pulp mill produces considerable amounts of organic by-products in the cooking liquors, often in quantities exceeding the amount of pulp produced. This broad spectrum of organic compounds may potentially be processed to valuable chemical products within pulp mill biorefineries, utilising the energy surplus of the pulp production for the manufacture.

Kraft pulp mills typically operate by pulping chipped lignocellulosic material using white liquor, an aqueous solution comprising sodium hydroxide and sodium sulfide. The white liquor removes lignin and hemicellulose from the lignocellulosic material, giving a cellulose pulp and black liquor comprising the white liquor components plus leached lignin and hemicellulose. The black liquor is concentrated and tall oil soap is skimmed. After further concentration and optional removal of a lignin fraction, the black liquor is combusted in the pulp mill recovery boiler, producing energy in the form of steam and electricity, as well as a slag comprising sodium carbonate and sodium sulfide. This slag is dissolved in process fluids to give a solution comprising sodium carbonate and sodium sulfide, known as green liquor. The green liquor is treated with calcium oxide (quicklime), regenerating a white liquor and giving a calcium carbonate precipitate (lime mud). The lime mud is calcined in lime kilns to regenerate quicklime. Thus, the overall mill process theoretically represents a closed cycle with respect to sodium, sulfur and calcium, although in practice some losses are obtained and the addition of make-up chemicals is required. Make-up chemicals are chemicals added to any stage of the pulping cycle in order to replenish and/or rebalance the chemical composition of the pulping chemicals. Typical make-up chemicals include sodium sulfate, sodium hydroxide or sodium carbonate.

Soda pulp mills operate by a similar closed cycle principle, although the recovery cycle differs somewhat. The main difference between soda pulping and kraft pulping is the pulping liquor: in a soda mill, soda liquor (aqueous sodium hydroxide) is used, which lacks sodium sulfide. The soda pulping process degrades the cellulose to a greater degree giving a weaker pulp. Therefore, kraft mills are the predominant form of pulp production.

The process of the present invention for producing organic acids may be integrated with a kraft mill or a soda mill. The process will now be described in further detail.

Process Overview

The process for producing an organic acid from a lignocellulosic feestock comprises a number of steps. The process is integrated with pre-existing pulp mill processes in order to recycle process streams, thus reducing chemical utilization, reducing waste, increasing energy production, and making the process for producing an organic acid from a lignocellulosic feedstock more economically viable and environmentally benign.

The process comprises the following steps: optional pre-hydrolysis of the lignocellulosic feedstock; alkaline pre-treatment of the lignocellulosic feedstock; optional oxidative delignification of the cellulose stream; saccharification and fermentation of the cellulose stream, either sequentially or simultaneously; and work-up and optional purification of the organic acid product. The streams derived from pre-hydrolysis and alkaline pre-treatment may optionally be processed to provide products derived from hemicellulose and lignin respectively. At least the spent alkaline pretreatment liquor is returned to the pulp mill for regeneration of alkaline liquor and energy generation. However, a number of further means of integration with pre-existing pulp mill processes are also feasible, as is made apparent in the following detailed process description.

Feedstock

Any lignocellulosic feedstock known in the art may be used. Such lignocellulosic feedstocks include, but are not limited to, wood, grass, bagasse, straw, plant material, paper, and combinations thereof. Suitable woods include both softwoods and hardwoods. The softwood tree species can be for example, but are not limited to: spruce, pine, fir, larch, cedar, and hemlock. Examples of hardwood species include, but are not limited to: birch, oak, poplar, beech, eucalyptus, acacia, maple, alder, aspen, gum trees and gmelina. The feedstock may comprise a mixture of different softwoods, e.g. pine and spruce. The feedstock may also comprise a non-wood raw material, such as bamboo, sugar beet pulp, wheat straw, soy hulls and bagasse. The raw material may also be a mixture of at least two of softwood, hardwood and/or non-wood.

Since the process is performed in close integration with a paper mill, feedstocks obtainable in proximity to, or in conjunction with, a paper mill may be preferable. Such feedstocks include pulpwood and forestry residues.

Forestry residues may be screened to reject fractions not suitable for further processing to organic acids. Such non-suitable forestry residue fractions, such as pins and sticks, may be combusted in the bark boiler of the pulp mill to provide steam and electricity.

The feedstock may be chipped to a suitable size prior to further processing.

Pre-Treatment

The goals of the pretreatment steps are to fractionate the lignocellulose feedstock into process streams suitable for further upgrading, and to provide a cellulose feed that can readily be converted to organic acids by the saccharification and fermentation steps.

Lignocellulosic feedstocks comprise significant quantities of hemicellulose. The presence of hemicellulose in the saccharification and fermentation feed means that enzymes capable of breaking down hemicellulose and microorganisms capable of fermenting the resulting C5 sugars are required if significant quantities of unprocessed hemicellulose are not to be obtained in the product organic acid stream. This means that microorganisms developed for use in current commercial methods utilizing starchy feedstocks may need to be replaced or supplemented. Moreover, the presence of hemicellulose or hemicellulose byproducts in the fermentation step may inhibit the production of organic acids from cellulose, thus lowering the product yield and/or purity. A high purity product stream is essential for commercial viability, in order to limit the costs for further purification of the organic acid products.

An initial pre-hydrolysis step may be performed on the lignocellulosic feedstock in order to substantially remove the hemicellulose fraction. No pre-hydrolysis is necessary however, and an alkaline pretreatment step may be performed directly on the raw lignocellulosic feedstock.

Pre-hydrolysis may be performed by cooking the lignocellulosic feedstock in aqueous solution. The pre-hydrolysis solution may have a regulated ionic strength by addition of alkali metal carbonate to the solution, for example at a $[CO_3^{2-}]$ concentration of 0.1 mol/l. The cooking temperature may be from 140° C. to 200° C., preferably between 160-180° C., and the cooking time may be from 30 minutes up to 2 hours. The temperature may be slowly ramped up to the cooking temperature after an impregnation period that may last up to 1 hour. After the pre-hydrolysis, the pre-hydrolysate is removed prior to the alkaline pre-treatment step. The pre-hydrolysate contains hemicellulose and C5 sugars that may be subjected to further valorisation steps.

After the optional pre-hydrolysis step, the lignocellulosic feedstock is subjected to an alkaline pre-treatment in order to provide a substantially pure cellulose stream suitable for further conversion into the desired organic acid; i.e. lignin and any hemicellulose not removed by a pre-hydrolysis step is removed at the pre-treatment stage.

The alkaline pre-treatment step is performed by cooking the lignocellulosic feedstock in an alkaline liquor from the pulp mill, otherwise termed an alkaline pre-treatment liquor. The most suitable alkaline liquor for use depends on a number of factors including the nature of the lignocellulosic feedstock, whether the lignin stream from the pre-treatment step is to be subject to further valorisation, and if so, whether low-sulfur lignin is desired.

Soda liquor (aqueous NaOH) may be used as the alkaline pre-treatment liquor. Soda liquor has the advantage that it is substantially free from sulfur and therefore the lignin obtainable after the pre-treatment is also substantially free from sulfur. The soda liquor may be obtained from a number of pulp-mill related sources.

In a soda pulp mill, soda liquor is the pulping liquor and is therefore readily available in vast quantities.

In a kraft pulp mill, soda liquor is obtainable by electrolysis of dust from the electrostatic precipitator of the pulp mill recovery boiler (ESP-dust). ESP-dust comprises mostly $Na_2SO_4$, which can be converted to NaOH and $H_2SO_4$ by electrolysis. Other anions such as chloride and carbonate, or cations such as potassium, may be removed from the ESP-dust prior to electrolysis. Methods of purification of ESP-dust, such as pulse filtration and ion exchange, are known in the art. By using ESP-dust as the source of the soda liquor, several advantages are obtained. A substance that is normally purged from the pulp mill process (ESP-dust) can instead be used to provide not only the soda liquor required in the alkaline pre-treatment, but also sulfuric acid which is used in subsequent process steps. The Na/S ratio of the pulp mill white liquor must be controlled carefully. By purging a portion of the gypsum ($CaSO_4$) formed during the manufacture of an organic acid, while returning the sodium to the pulp mill recovery process, the Na/S ratio is rebalanced, reducing the need for expensive NaOH makeup to the pulp mill.

The NaOH make-up normally added to the kraft pulp mill white liquor may also be used as the soda liquor in the pre-treatment process. However, the quantity of NaOH make-up normally added to the white liquor in a typical pulp mill may in some cases be insufficient by itself to support production of an organic acid on a commercially viable scale.

White liquor from the kraft pulp mill may be utilized as the alkaline pre-treatment liquor. This has the advantage that white liquor is already abundant at the pulp mill and therefore no new processes need be implemented for production of the alkaline pre-treatment liquor. Pre-treatment with white liquor is milder than treatment with soda liquor and therefore may provide greater yields of a cellulose feed suitable for saccharification and fermentation in some instances, depending on feedstock. However, pre-treatment using white liquor results in a sulfur-containing lignin stream. In many circumstances the presence of sulfur in the lignin is non-problematic, but if sulfur-free lignin is desired, a pretreatment liquor comprising less sulfur should be used. Such a liquor may be soda liquor, or alternatively, white liquor may be oxidised by known methods in order to avoid sulfur in the lignin product. Use of white liquor as the alkaline pre-treatment liquor may lead to a somewhat greater demand for NaOH make-up in the pulp mill.

The alkaline pre-treatment liquor may be a combination of liquors from a variety of sources. For example, a blend of white liquor and soda liquor may be used. The soda liquor may itself comprise a blend of NaOH make-up liquor and liquor derived from electrolysis of ESP-dust. A proportion of black liquor from the pulp mill or pretreatment step may also be used in the alkaline pre-treatment liquor.

The alkaline pre-treatment step may be performed by cooking the lignocellulosic feedstock in the alkaline liquor. The cooking temperature may be from 140° C. to 190° C., preferably from 150° C. to 180° C. The cooking time may be from 30 minutes up to four hours. After alkaline pre-treatment, the process stream is separated into a pretreated cellulosic feed and a black liquor stream.

The pretreated cellulosic feed may optionally be subjected to an oxygen delignification step prior to undergoing saccharification and fermentation. The oxygen delignification may be performed in a single stage or as two-stages. The temperature for delignification may be from 80° C. to 110° C. and the time required may be from 30 minutes to three hours. The use of an oxygen delignification step may in some cases provide a purer feed to the saccharification and fermentation steps, resulting in a lesser need for purification of the organic acid product and therefore an improved overall process economy.

Saccharification and Fermentation

The saccharification (hydrolysis) and fermentation of the cellulosic feed converts cellulose, and possibly any hemicelluloses present in the feed, to the desired organic acid in two stages. The first stage is the enzymatically catalysed hydrolysis of cellulose to fermentable sugars, primarily glucose. Depending on the enzyme preparation used, any hemicelluloses present in the reaction mixture may also be hydrolysed to sugars, primarily a mixture of C5 and C6 sugars.

Suitable enzyme preparations include, but are not limited to, cellulase preparations, hemicellulase preparations, cellobiase preparations, xylanase preparations, amylase preparations, pectinase preparations, or enzyme preparations comprising a mixture of such enzymes. Preparations intended for the saccharification of lignocellulose feeds and comprising a mixture of cellulases and hemicellulases are commercially available. One such preparation is for example marketed by Novozymes under the name Cellic® CTec3.

The second stage is the fermentation of the sugars by one or more suitable microorganisms to provide the desired organic acid product. The obtained organic acid depends on the microorganism(s) used.

Organic acids that may be obtained by the saccharification and fermentation process include, but are not limited to, lactic acid, acetic acid, citric acid, itaconic acid, succinic acid, fumaric acid, glycolic acid, pyruvic acid, acetic acid, glutamic acid, malic acid, maleic acid, propionic acid, butyric acid, gluconic acid and combinations thereof. The saccharification and fermentation product is preferably lactic acid or acetic acid, even more preferably lactic acid.

The microorganism used in the fermentation may be a bacterium, a fungus, a yeast, an archaea or an algae. The microorganism is preferably a bacterium of the genus *lactobacillus* if lactic acid is to be produced, or a bacterium of the genus *acetobacterium* if acetic acid is the desired product.

The saccharification and fermentation may be performed sequentially (SHF) or simultaneously (SSF). If performed sequentially, each stage may be performed in a separate reactor, with optional further processing of the obtained saccharide feed between stages. Alternatively, the stages can be performed sequentially but in a single reactor, by addition of a microorganism to the enzymatic hydrolysis reaction mixture.

Preferably, the saccharification and fermentation are performed simultaneously, as a simultaneous saccharification and fermentation (SSF). SSF has the advantages of a less capital equipment required as compared to two-reactor methods, and a reduced risk of product inhibition of enzyme activity.

The SSF step may be performed by stirring a slurry of the cellulosic stream together with a suitable enzyme preparation and microorganism as described above. Suitable concentrations and conditions depend on a number of parameters including the nature of the feedstock, pre-treatment, enzyme and microorganism used. The pH of the cellulosic feed may be adjusted prior to the SSF step in order to optimise the rate of organic acid formation. This can for example be performed by addition of suitable quantities of sulfuric acid. During fermentation the pH of the reaction mixture is lowered by formation of the organic acid, leading to inhibition of the microorganism. This is countered by addition of calcium oxide obtained from the pulp mill in order to maintain the pH of the mixture within the optimal pH operating window. Addition of calcium oxide gives the calcium salt of the organic acid, e.g. calcium lactate or calcium acetate.

In order to reduce the quantities of calcium oxide required, the SSF step may be initiated using only a partial quantity of the cellulosic feed, adjusted to a suitable pH. As organic acid is formed during the SSF step, the corresponding lowering of the pH may be countered by periodic or continuous addition of cellulosic feed having basic pH, i.e cellulosic feed that is non-pH adjusted.

Gypsum Precipitation

After the production of the organic acid, the product stream must be purified. The initial step in purification is addition of sulfuric acid in quantities sufficient to retrieve the free organic acid from the calcium salt. The resulting calcium sulfate (gypsum) is substantially insoluble in the aqueous medium and precipitates. The gypsum precipitate is removed, for example by filtration or centrifugation, thus providing a relatively pure aqueous solution of organic acid. In some cases the product may be sufficiently pure and concentrated for the intended purpose, otherwise further purification and concentration as described below may be necessary.

The gypsum isolated by precipitation may be returned to the pulp mill where it is integrated with the chemical recovery cycle for regeneration to calcium oxide. This may for example be performed by adding the gypsum to the pulp mill green liquor. The green liquor is then recausticized by addition of calcium oxide to provide white liquor and lime mud (calcium carbonate). The lime mud is then calcined in the lime kiln to regenerate the calcium oxide. Thus, the pulp mill recovery process is essentially a closed cycle for Na, Ca and S, although some losses do occur and make-up chemicals must therefore be added as required.

If the sulfuric acid used to precipitate gypsum is intrinsic to the pulp mill, i.e. is derived from the pulp mill process chemicals such as ESP-dust, then returning the gypsum to the pulp mill recovery cycle will have a negligible impact on the pulp mill Na/S ratio. However, if extrinsic sulfuric acid (i.e. sulfuric acid not deriving from the pulp mill process chemicals) is used to form and precipitate the gypsum, integration of the gypsum in the pulp mill recovery cycle will affect the Na/S balance of the pulp mill process. In some cases this may be desirable, and reduces the need for addition of other sulfur make-up chemicals such as elemental sulfur or salt cake to the pulp mill processes. In other cases, the Na/S balance may be negatively affected by the return of gypsum, meaning that additional NaOH make-up may be required to rebalance the Na/S ratio.

Purification and Concentration

If the dilute organic acid obtained after precipitation of gypsum is insufficiently pure or concentrated, further purification steps may be performed.

The dilute organic acid may for example be purified by reactive distillation with a simple alcohol such as methanol or ethanol in order to provide the organic acid alcohol ester, e.g. methyl acetate or methyl lactate. The isolated ester may then be subjected to hydrolysis to provide the original organic acid in a purer, more concentrated form. The alcohol recovered may be re-used in the reactive distillation, and therefore the process is overall a closed cycle with regard to the alcohol. Other operations such as filtration, extraction, electrodialysis and evaporation may be performed as required in order to obtain a product with the desired properties.

Lignin Recovery

If desired, lignin may be recovered from the spent pretreatment (black) liquor. The market for lignin is expanding, and extensive research regarding valorisation of lignin product streams is ongoing. Moreover, if the capacity of a pulp mill is limited by the throughput capacity of its recovery boiler, then removal of lignin from black liquor can reduce the load on the recovery boiler, thereby increasing the overall capacity of the plant. The isolated lignin may be sold or used to replace fossil fuel when firing the pulp mill lime kilns.

The black liquor from the pretreatment may be combined with black liquor from the pulp mill and processed together with the pulp mill black liquor. This is particularly suitable if the pretreatment is performed using white liquor, since the resulting lignin is essentially indistinguishable from regular kraft lignin. Alternatively, the black liquor from the pretreatment may be processed in isolation. This is especially suitable if pre-treatment is performed using soda liquor and it is desired to isolate the resulting sulfur-free lignin. Sulfur-free lignin may potentially command a premium price in applications where the presence of sulfur in the lignin is considered problematic. Such applications may include use as solid fuel (where no flue scrubbing is available), as a food additive, or as a precursor to carbon fiber.

Lignin may be recovered from black liquor using any method known in the art. Such methods include, but are not limited to the Lignoboost process, the Lignoforce process, the SLRP (Sequential Liquid-Lignin Recovery and Purification) process, and membrane filtration methods. In short, the Lignoboost process involves taking a stream of concentrated black liquor from the black liquor evaporators. Lignin is precipitated from the concentrated black liquor by acidification, preferably using carbon dioxide. The precipitated lignin is isolated by filtration, re-dispersed and the dispersion is acidified. The resulting slurry is then filtered and washed.

Tall oil soap may be skimmed from the black liquor prior to precipitation of lignin. Other known means and methods for isolating kraft lignin may alternatively be used.

After optional lignin removal the black liquor is conveyed to the recovery boiler of the pulp mill, providing steam, electricity and recovering the pulping/pretreatment white liquor by the pulp mill recovery cycle. The pulp mill may use alternative chemical recovery technologies, such as black liquor gasification, to recover the pulping chemicals.

Hemicellulose Utilisation

If the lignocellulosic feed is subjected to a pre-hydrolysis step, a pre-hydrolysate rich in hemicellulose and C5 sugars is obtained. This pre-hydrolysate may be subjected to treatment in order to recover potentially valuable product fractions such as xylose and furfural. Such treatments may include membrane filtration and/or hydrolysis of hemicelluloses.

The process described herein may be performed in a fully integrated manner with pre-existing pulp mill processes, meaning that all process streams and resides are returned to the pulp mill for chemical and energy generation. Thus, the process is essentially closed-cycle with regard to process chemicals such as calcium oxide and alkaline liquor. The biomass feedstock is processed to valorised products, and all residues may be used to generate energy in the form of steam and electricity production. Thus, the process herein described, by being integrated with pulp mill processes, provides an economically viable and green method of obtaining organic acids from abundant renewable lignocellulosic feedstocks.

EXAMPLES

Feedstocks tested in the examples were eucalyptus pulpwood (*E. urograndis*), short-rotation eucalyptus, Scots pine forestry residues, and energy cane. The feedstocks were chipped to a suitable size prior to processing.

Pre-Treatment

Figure 1:
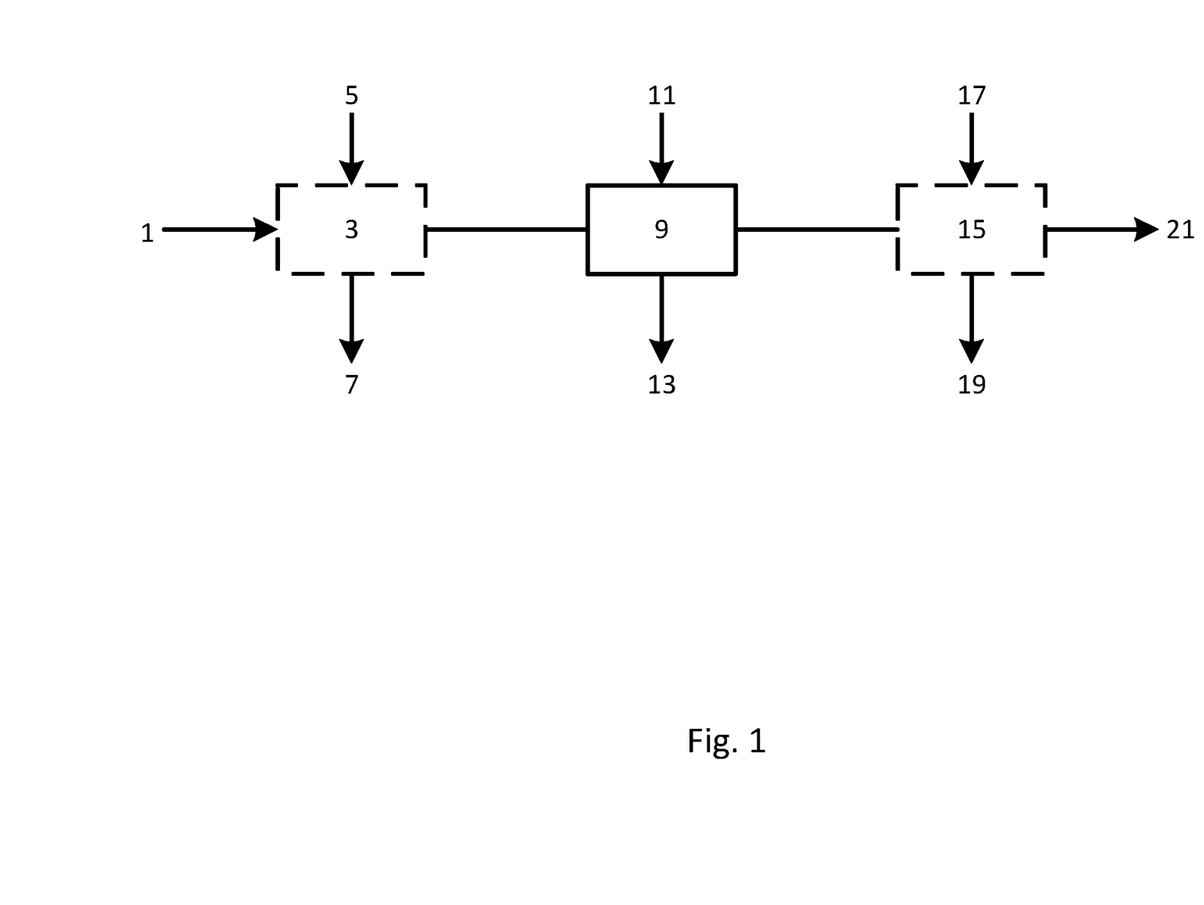
FIG. 1 schematically illustrates the pretreatment steps for the lignocellulosic feedstock according to the present invention.

FIG. 1 illustrates schematically the pretreatment steps for the lignocellulosic feedstock. The feedstock 1 is first subject to an optional pre-hydrolysis step 3 using water 5 as the pre-hydrolysis liquor and obtaining a pre-hydrolysate 7. The lignocellulosic feedstock then undergoes a pretreatment step 9 with an alkaline pretreatment liquor 11. This gives a black liquor 13 and a pretreated cellulose feed. The pretreated cellulose feed is subjected to an optional oxygen delignification step 15 using an alkaline liquor 17, giving a spent liquor 19 and a cellulosic feed 21 suitable for further processing.

Tested pre-hydrolysis conditions for a range of feedstocks are outlined in Table 1.

TABLE 1

| Type of biomass | Eucalyptus urograndis | | | Pine Forest Residues | | Energy Cane |
|---|---|---|---|---|---|---|
| Amount charged biomass, dry weight (kg$_{100}$) | 1.25 | 2.5 | 46 | 0.25 | 2.0 | 0.1 |
| Type of digester | Forced circulation | | Autoclave | Forced circulation | | Autoclave |

TABLE 1-continued

| Type of biomass | Eucalyptus urograndis | | | Pine Forest Residues | | Energy Cane |
|---|---|---|---|---|---|---|
| Liquor-to-wood/material ratio (L/kg) | 6 | | 5.3 | 6 | 6 | 14 |
| Time to temperature (min) | 64 | | 50 | 63 | 53 | 64 |
| Temperature (° C.) | 160 | | | 180 | 175 | 160 |
| Time (min) | 60 | 0-60 | 30-40 | 0-90 | 90 | 45 |

Table 2 outlines the tested pre-treatment conditions and the results of the pre-treatment for the eucalyptus feedstocks. It can be seen that using partially oxidised white liquor allows a substantial reduction in cooking time.

TABLE 2

| | Cook type | | | |
|---|---|---|---|---|
| Feedstock | Oxidised White liquor Pulpwood | Soda Pulpwood | Soda Short rotation | Soda Pulpwood |
| Alkali charge, EA % | 20.5 | 21.5 | 21.5 | 22.5 |
| Initial HS-, mol/L | 0.02 | 0 | 0 | 0 |
| Cooking time, min | 85 | 190 | 190 | 190-195 |
| Residual alkali, g/L | 6.9 | 6.3 | 8.2 | 8.1 +/− 1.7 |
| Alkali consumption, kg/ton | 177.3 | 190 | 182.4 | 190 +/− 10 |
| Kappa number | 15.3 | 14.5 | 10.6 | 10 +/− 0.5 |
| Reject, % on wood | 0.1 | 0.2 | 0.1 | 0.1 |
| Total yield, % on wood | 44.1 | 42.1 | 43.0 | 39.4 |
| Dry Solids hydrolysate (wt %) | 1.4 | 1.4 | 2.0 | 1.95 |
| End-pH hydrolysate | 3.9 | 3.2 | 3.3 | 3.1 |
| Dry Solids Black Liquor (wt %) | 16 | 14.4 | 14.1 | 13.9 |

Table 3 outlines the tested pre-treatment methods and results for the pine forestry residue feedstock. It can be seen that pre-treatment with white liquor provides a greater total yield and that a greater proportion of hemicellulose is retained in the pulp.

TABLE 3

| Pretreatment method | White liquor | Soda |
|---|---|---|
| Xylan % on pulp | 12 | 2.2 |
| Glucomannan % on pulp | 6.6 | 0.7 |
| Cellulose % on pulp | 75 | 91 |
| Acid-insoluble lignin % on pulp | 4.4 | 4.3 |
| Acid-soluble lignin % on pulp | 0.7 | 0.4 |
| Extractives % on pulp | 0.5 | 1.1 |
| Ash content % on pulp | 0.7 | 0.5 |
| Total yield after cooking % on wood | 37.6 | 24.1 |

Table 4 outlines the tested pre-treatment methods for energy cane feedstock.

TABLE 4

| Pretreatment method | Soda | Soda + O2 delignification |
|---|---|---|
| Kappa number | 13.1 | 5.5 |
| Total yield | 45.6 | n.d |
| Alkali consumption, kg/ton | 200 | |

TABLE 4-continued

| Pretreatment method | Soda | Soda + O2 delignification |
|---|---|---|
| Ash content, % | 2.7 | ~2 |
| Lignin, % on pulp | 2.7 | n.d. |

Thus, it can be seen that a range of pre-treatment methods using pulp mill chemicals can be applied to the lignocellulosic feedstocks.

Hydrolysis and Fermentation

Pulps from *Eucalyptus urograndis* and Scandinavian softwood were evaluated as the substrate and *Lactobacillus* bacteria were selected as the fermenting microorganisms. Cellic® CTec3 from Novozymes was used as the hydrolytic enzyme preparation. Separate hydrolysis and fermentation (SHF) experiments were initially performed on laboratory scale.

The pretreated eucalyptus was readily enzymatically hydrolysed into high concentrations of glucose which in turn enabled high concentrations of lactic acid. High product titer and "clean" or noncomplex substrates is a key aspect for downstream processing. Using relatively pure and noncomplex feedstock with high cellulose content, such as pulp, could therefore be advantageous compared to using more complex feedstock such as dilute-acid pre-treated or steam exploded lignocellulosic material.

In the fermentation step, very high titers of lactic acid (143 g/L) and good yields (0.98 g lactic acid/g consumed glucose) were achieved using a *Lactobacillus* mixed culture. The *Lactobacillus* bacteria performed better when grown on the pulp hydrolysate compared to a glucose-based reference medium.

Figure 2:
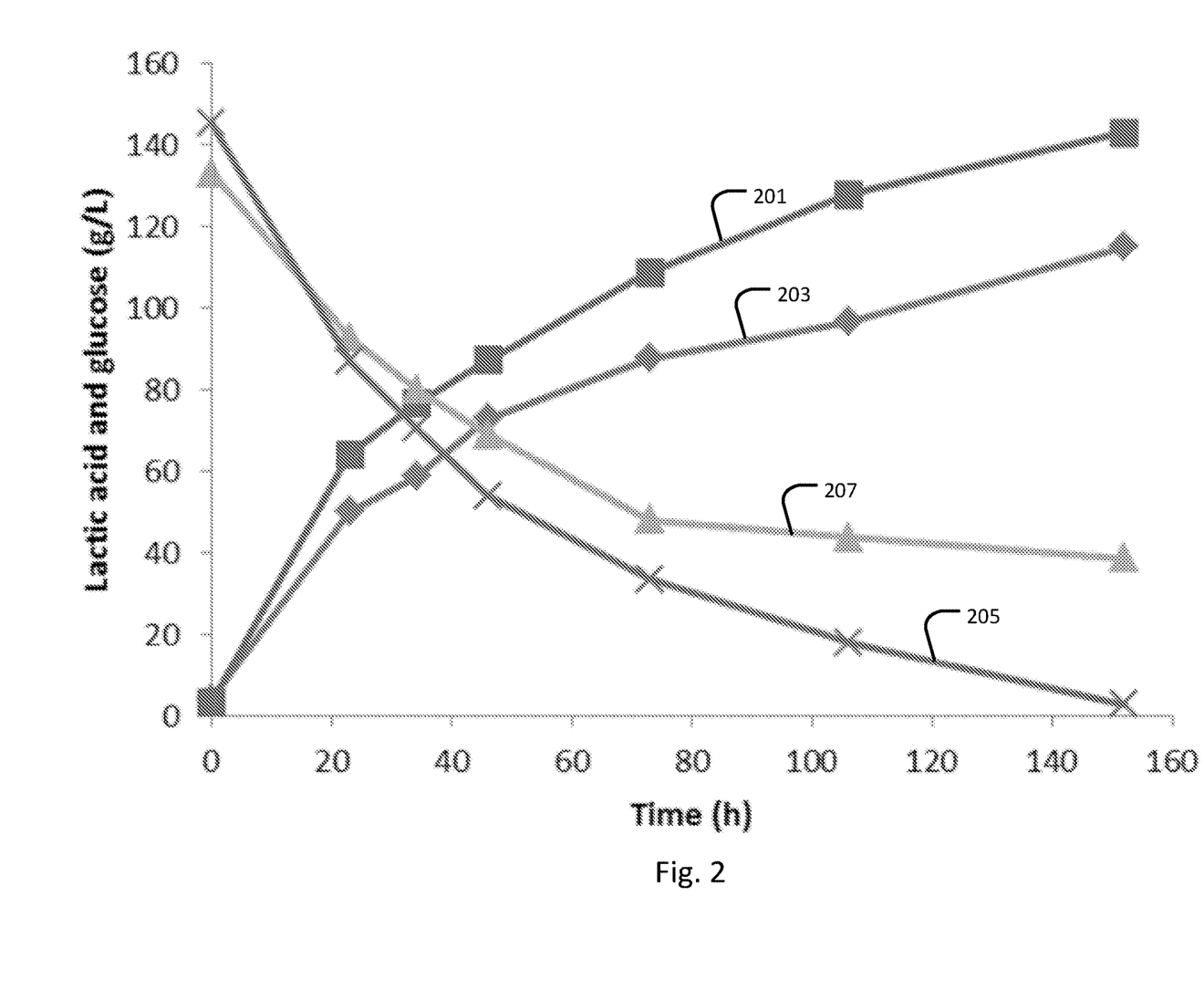
FIG. 2 is a chart providing a comparison between *eucalyptus* pulpwood hydrolysate and a glucose reference medium as a fermentation medium for the production of lactic acid.

FIG. 2 shows a comparison between eucalyptus pulpwood hydrolysate and a glucose reference as the fermentation medium. It can be seen that production of lactic acid from the eucalyptus hydrolysate (line 201) proceeds at a greater rate as compared to lactic acid production from the glucose reference medium (line 203). A greater final lactic acid concentration is obtained from the eucalyptus hydrolysate. Looking at the glucose concentration, it can be seen that the eucalyptus hydrolysate is more-or-less fully converted (line 205), whereas a significant proportion of the glucose reference remains unconverted (line 207).

A simultaneous saccharification and fermentation (SSF) experiment on a 50 litre pilot bioreactor scale resulted in a concentration of 107 g/L lactic acid after 98 h using a pretreated eucalyptus feed concentration of 15% dry solids and an enzyme concentration of 6% (g CTec3/dry solids). The addition of 2% additional enzyme at 98 h did not result in a large increase in lactic acid production. The final lactic acid concentration was 114 g/L after 123 h, the yield was 0.76 g lactic acid per g feed and the productivity was 0.91 g/L/h. In this pilot scale test, pH was adjusted during cultivation using $NH_4OH$ (25 wt %) and $H_2SO_4$ (2M). The consumption of $NH_4OH$ and $H_2SO_4$ for pH adjustment during cultivation was 3.75 litre and 50 mL, respectively.

Both the SHF (separate hydrolysis and fermentation) and SSF (simultaneous saccharification and fermentation) experiments resulted in a mixture of D- and L-lactic acid.

Integrated Process

Figure 3:
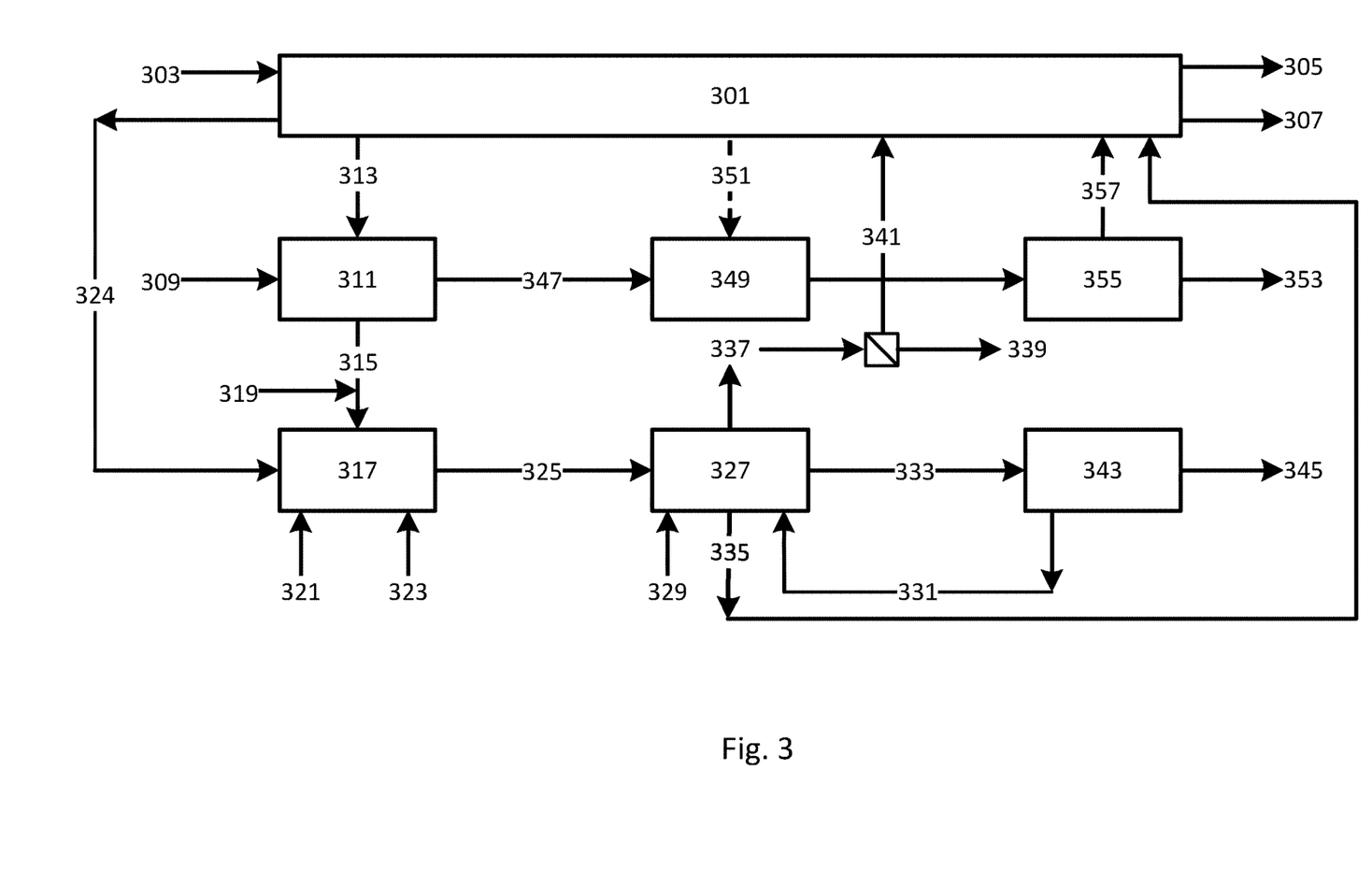
FIG. 3 schematically illustrates the integration of the pulp mill process with the process for the production of an organic acid.

FIG. 3 shows a schematic overview of the process for producing an organic acid integrated with a pulp mill process. A pulp mill 301 has a first lignocellulosic feedstock 303 as an input and produces pulp 305 and electricity 307. The organic acid production process runs parallel to the pulp mill process. A second lignocellulosic feedstock 309 is provided to an alkaline pretreatment step 311. An alkaline liquor 313 is obtained from the pulp mill as a process chemical in the pretreatment step. The alkaline liquor 313 may be selected from liquors including, but not limited to, white liquor, soda liquor, or mixtures therefore. Following the alkaline pretreatment step 311, the pretreated feedstock 315 is transferred to a SSF step 317, optionally being neutralised by the addition of an acid 319 prior to commencement of the SSF stage. Further inputs to the SSF stage 315 are saccharification enzymes 321, fermentation microorganisms 323, and calcium oxide 324 obtained from the pulp mill. After the SSF stage 317 the obtained raw product 325 is transferred to a purification stage 327, including the steps of precipitation and esterification. Inputs to the purification stage 327 are sulfuric acid 329, optionally obtained from the pulp mill ESP dust, and alcohol 331. Outputs from the purification stage are, besides the esterified acid 333, organic residues 335 including lignin and biomass which are transferred to the pulp mill for energy recovery, and precipitated gypsum 337. A portion 339 of the precipitated gypsum stream is purged, whereas a further portion 341 of the gypsum steam is returned to the chemical recovery cycle of the pulp mill in order to recover calcium oxide. The esterified acid 333 is hydrolysed in a final step 343 to provide pure acid product 345 and recover alcohol 331 for use in the purification stage.

The hydrolysate 347 from the alkaline pretreatment stage 311 is transferred to an evaporation stage 349. Here it may optionally be combined with black liquor 351 from the pulp mill. Lignin 353 is then recovered from the evaporation product in an lignin precipitation stage 355. Residues 357 from this stage are returned to the pulp mill 301 for chemical and energy recovery.

Figure 4:
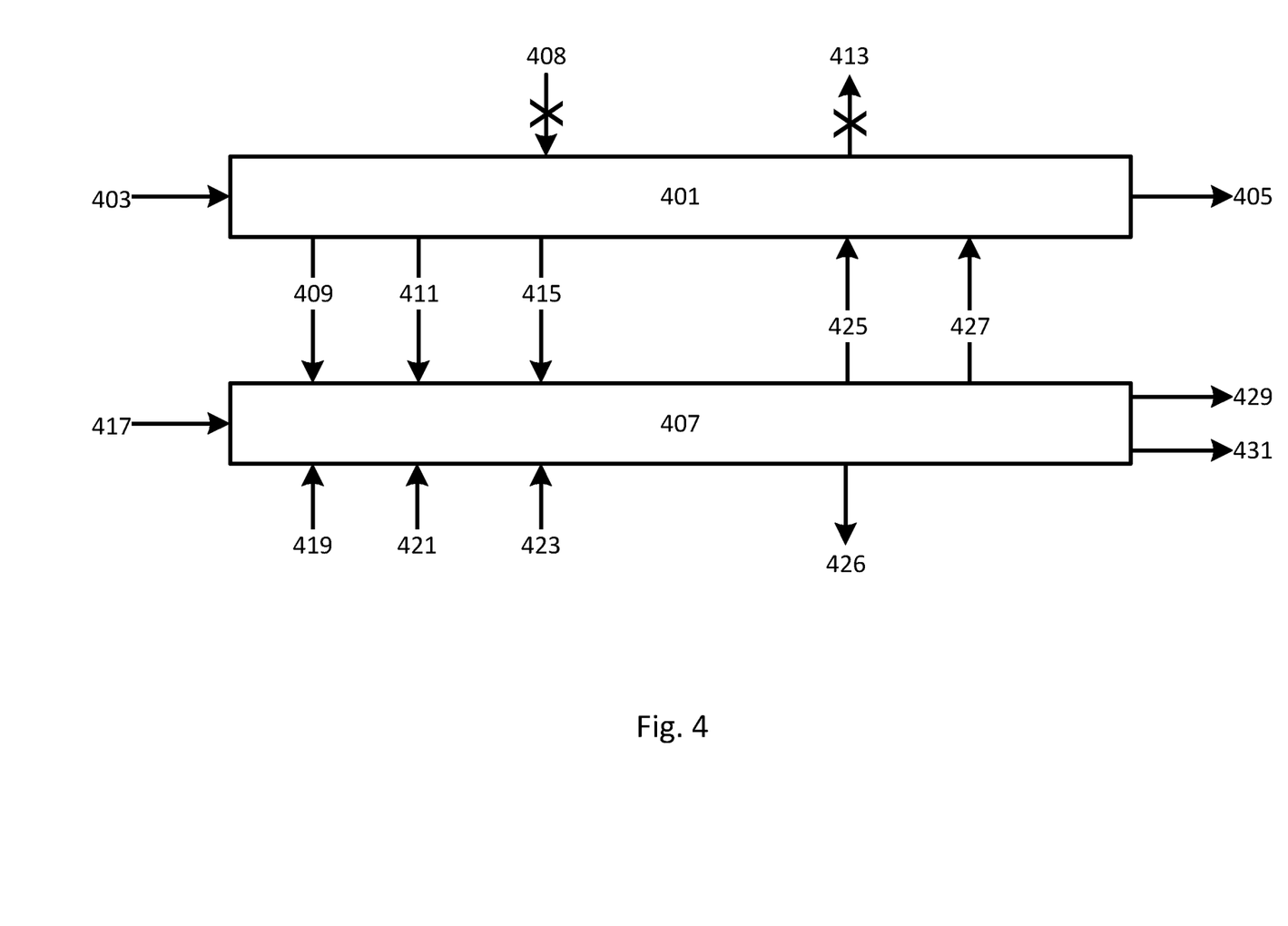
FIG. 4 schematically illustrates a potential mass balance of the integrated pulp mill and organic acid production processes when soda liquor is used as the alkaline pretreatment liquor.

FIG. 4 shows a schematic mass balance for a pulp mill and integrated organic acid production line using soda liquor and sulfuric acid derived from ESP dust as process chemicals in the organic acid production line.

The pulp mill 401 is shown with a regular wood chip input 403 and pulp output 405. Integration with the organic acid production line 407 means that the need for purging of ESP dust 413 is greatly reduced. The requirement for NaOH make-up 408 to the mill is also greatly reduced or avoided completely. Instead, the pulp mill ESP dust can be converted to sodium hydroxide 409 and sulfuric acid 411 that are provided as inputs to the organic acid (OA) line 407. Calcium oxide 415 is also taken from the pulp mill 401 for use in the OA line 407. Thus, the majority of the process chemicals required for the OA line are obtained from the pulp mill. Lignocellulosic feedstock 417 is provided to the OA line. This lignocellulosic feedstock 417 may be pulpwood, but may also comprise rejects from the pulp mill or forestry residues not suitable for conventional pulp production. Further inputs to the OA line 407 are enzymes 419, carbon dioxide 421, and sulfuric acid make-up 423.

With regard to process outputs, end products of the OA line are the organic acid 429, such as lactic acid or acetic acid, and sulfur-free lignin 431. By-products of the organic acid production process are mostly returned to the pulp mill for recycling or energy generation. A first portion 425 of the gypsum produced in the OA line is returned to the pulp mill 401 for integration with the mill regeneration cycle, whereas a second portion 426 of the gypsum produced is purged. The purged portion 426 is typically less than the recycled portion 325. Filtrates and residues 427 from the OA line are also returned to the pulp mill for regeneration of pulping/pretreatment chemicals and energy generation. It can be seen from the schematic mass balance that very little excess chemical input is required for the OA production line and very little non-regenerable waste is produced.

Figure 5:
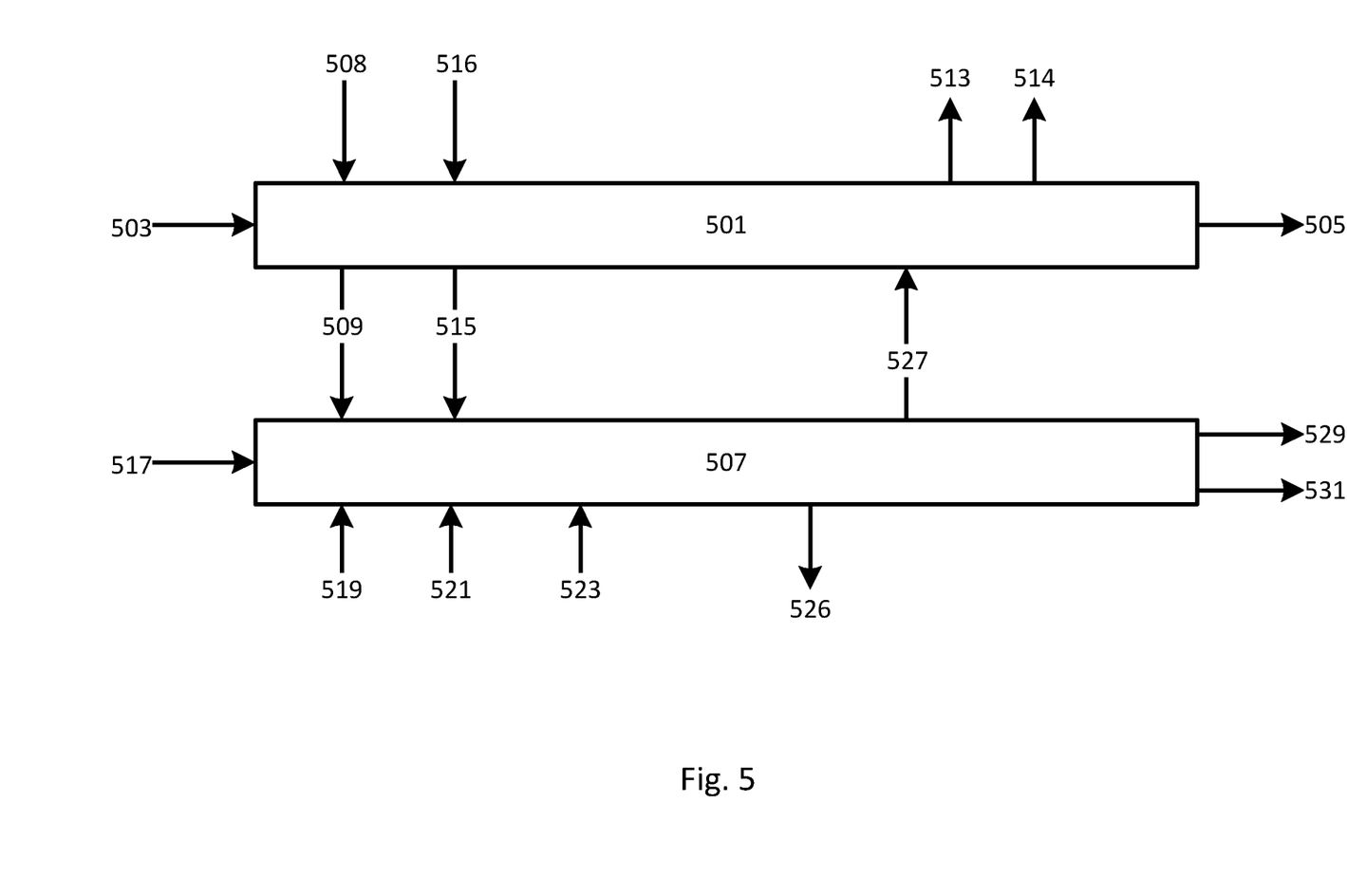
FIG. 5 schematically illustrates a potential mass balance of the integrated pulp mill and organic acid production processes when white liquor is used as the alkaline pretreatment liquor.

FIG. 5 shows a schematic mass balance for a pulp mill and integrated organic acid production line using white liquor as the pretreatment liquor for the organic acid (OA) line.

The pulp mill 501 is shown with a regular wood chip input 503 and pulp output 505. White liquor 509 and calcium oxide 515 are provided to the organic acid production line 507 as process chemicals. This results in an increased requirement for NaOH make up 508 and CaO make up 516 to the pulp mill.

Lignocellulosic feedstock 517 is provided to the OA line 507. This lignocellulosic feedstock 517 may be pulpwood, but may also comprise rejects from the pulp mill or forestry residues not suitable for conventional pulp production. Forestry residues not suitable for use in the OA line may be diverted to the bark boiler of the pulp mill in order to further increase electricity production. Further inputs to the OA line 507 are enzymes 519, carbon dioxide 521, and sulfuric acid 523.

With regard to process outputs, end products of the OA line are the organic acid 529, such as lactic acid or acetic acid, and lignin 531. In order to maintain the sulfur balance of the pulp mill, gypsum 526 produced during the organic acid production is purged. However, further filtrates and residues 527 from the OA line are returned to the pulp mill for regeneration of pulping/pretreatment chemicals and energy generation. This results in a somewhat increased production of ESP dust 513 in the pulp mill, but provides much increased electricity production 514. Again, it can be seen from the schematic mass balance that relatively little non-regenerable waste is produced.

The invention claimed is:

1. A process for the production of an organic acid from a lignocellulosic feedstock, wherein the process is integrated with a pulp mill and comprises the steps:
   a) providing a lignocellulosic feedstock;
   b) obtaining an alkaline liquor from the pulp mill;
   c) pre-treating the lignocellulosic feedstock with the alkaline liquor, thereby obtaining a pretreated cellulosic feed and a black liquor;
   d) obtaining calcium oxide from the pulp mill;
   e) subjecting the pretreated cellulosic feed from step c) to enzymatic hydrolysis, thereby obtaining a saccharide feed;
   f) subjecting the saccharide feed from step e) to microbial fermentation using the calcium oxide from step d) as a neutralising agent, thereby obtaining an organic acid calcium salt;
   g) treating the organic acid calcium salt with sulfuric acid, thereby obtaining gypsum and the organic acid;
   h) optionally isolating lignin from the black liquor obtained in step c), thereby obtaining lignin and weak black liquor; and
   i) returning the black liquor obtained in step c) and/or the weak black liquor obtained in step h) to the pulp mill for integration with the pulp mill chemical recovery process;
   wherein steps e) and f) are performed either sequentially or simultaneously.

2. The process according to claim 1 wherein steps e) and f) are performed simultaneously.

3. The process according to claim 1, wherein the organic acid is lactic acid, acetic acid, citric acid, itaconic acid, succinic acid, fumaric acid, glycolic acid, pyruvic acid, glutamic acid, malic acid, maleic acid, propionic acid, butyric acid, gluconic acid or combinations thereof.

4. The process according to claim 1, wherein the alkaline liquor comprises pulp mill white liquor and/or soda liquor.

5. The process according to claim 1, wherein the alkaline liquor and the sulfuric acid are at least in part derived from electrolysis of pulp mill electrostatic precipitator dust.

6. The process according to claim 5, wherein the alkaline liquor is essentially free from sodium sulfide.

7. The process according to claim 1, wherein the black liquor obtained in step c) is combined with pulp mill black liquor prior to isolating lignin in step h).

8. The process according to claim 1, wherein at least a portion of the gypsum obtained in step g) is returned to the pulp mill for integration with a pulp mill lime regeneration process.

9. The process according to claim 1, wherein the lignocellulosic feedstock from step a) is subjected to an aqueous prehydrolysis step prior to step b), thereby obtaining a prehydrolysed lignocellulosic feedstock and a hemicellulose hydrolysate.

10. The process according to claim 9, wherein a hemicellulose or a product derived from hemicellulose is isolated from the hemicellulose hydrolysate.

11. The process according to claim 1, wherein the organic acid obtained in step g) is purified by reactive distillation with an alcohol to provide an ester, followed by hydrolysis of the ester to provide a purified organic acid.

12. The process according to claim 1, wherein the pretreated cellulosic feed from step c) is subjected to an oxygen delignification step prior to step e).

13. The process according to claim 1, wherein at least part of the pretreated cellulosic feed from step c) is subjected to neutralisation by addition of sulfuric acid prior to step e).

14. The process according to claim 1, wherein the lignocellulosic feedstock is selected from the group consisting of wood, grass, bagasse, straw, plant material, paper, and combinations thereof.

15. The process according to claim 1, wherein all filtrates and residues from the process are returned to the pulp mill and integrated with the pulp mill chemical recovery process.

16. The process according to claim 1, wherein the pulp mill is an alkaline pulp mill.

* * * * *